United States Patent [19]

Green

[11] Patent Number: 5,398,861
[45] Date of Patent: Mar. 21, 1995

[54] DEVICE FOR DRIVING SURGICAL FASTENERS

[75] Inventor: David T. Green, Westport, Conn.

[73] Assignee: United States Surgical Corporation, Norwalk, Conn.

[21] Appl. No.: 48,455

[22] Filed: Apr. 16, 1993

[51] Int. Cl.⁶ ............................................. A61B 17/00
[52] U.S. Cl. ........................... 227/175; 227/19; 227/132; 227/146
[58] Field of Search ............... 227/19, 175, 132, 146

[56] References Cited

U.S. PATENT DOCUMENTS

| | | | |
|---|---|---|---|
| 1,601,324 | 9/1926 | Reynolds | 227/146 X |
| 2,767,399 | 10/1956 | Widener | 227/146 |
| 3,193,167 | 7/1965 | Newton | 227/132 |
| 3,618,447 | 11/1971 | Goins . | |
| 4,321,002 | 3/1982 | Froehlich . | |
| 4,448,194 | 5/1984 | DiGiovanni et al. . | |
| 4,451,254 | 5/1984 | Dinius et al. . | |
| 4,523,695 | 6/1985 | Braun et al. . | |
| 4,569,469 | 2/1986 | Mongeon et al. . | |
| 4,593,843 | 6/1986 | Saravis | 227/19 X |
| 4,682,412 | 7/1987 | Pfeffer | 227/132 X |
| 4,753,636 | 6/1988 | Free . | |
| 4,821,942 | 4/1989 | Richards et al. | 227/146 X |
| 4,869,242 | 9/1989 | Galluzzo . | |
| 4,873,976 | 10/1989 | Schreiber . | |
| 4,895,148 | 1/1990 | Bays et al. . | |
| 4,901,712 | 2/1990 | Voegell et al. | 227/147 X |
| 4,944,742 | 7/1990 | Clemow et al. . | |
| 4,976,686 | 12/1990 | Ball et al. . | |

FOREIGN PATENT DOCUMENTS

| | | | |
|---|---|---|---|
| 231522 | 3/1960 | Australia | 227/132 |
| 0471334 | 2/1992 | European Pat. Off. . | |
| 0477619 | 4/1992 | European Pat. Off. . | |
| 0392750 | 10/1992 | European Pat. Off. . | |
| 0558031 | 9/1993 | European Pat. Off. . | |
| 2368341 | 6/1978 | France | 227/132 |

Primary Examiner—Rinaldi I. Rada

[57] ABSTRACT

A device for driving surgical fasteners into tissue such as the menisci of the knee. The device essentially consists of a tubular housing member through which a piston shaft passes. The piston shaft extends at a first end and terminates in a gripping knob which facilitates retraction of the piston from the housing, and contacts a fastening member at a discharge end to drive the fastener from the device. A pivotable latching member engages the gripping knob when the piston arrangement is retracted against the force of the spring, and pivots to release the piston arrangement to fire the fastener.

15 Claims, 6 Drawing Sheets

DEVICE FOR DRIVING SURGICAL FASTENERS

BACKGROUND OF THE INVENTION

1. Field of the Invention

The present invention relates to an apparatus and method for repairing torn tissue, and in particular to a device for driving surgical fasteners to secure torn tissue such as the menisci of the knee.

2. Description of the Prior Art

The menisci are crescent-shaped disks positioned in the knee and attached to the joint capsule and serve as buffers between the bones of the femur and the bones of the tibia and fibula. Surgical repair of the menisci is generally performed arthroscopically and requires precision instruments to perform the procedure in a limited space so that damage to the surrounding tissue and muscle is limited.

Surgical procedures for repairing torn meniscal tissue have been developed which utilize sutures, barbed fasteners or tacks which are driven through the tissue and across the tear to anchor the sides of the tear in abutting relation to facilitate healing.

One type of prior art barbed fasteners and fastener appliers is described in U.S. Pat. No. 4,976,715 to Bays et al. Bays et al. discloses a hollow tack member having a series of outwardly projecting barbed members and which terminates in a flange portion which prevents over-insertion of the tack into the tissue. The tack is hollow to permit the passage of a surgical needle therethrough, and the needle is attached to an applicator for forcibly pushing the tack through the tissue to anchor sides of a tear in the tissue.

Also known in the prior art are surgical stapling and fastening devices which drive tissue grasping staples to surgically close incisions or wounds. However, these devices generally require large working areas in that the device must surround or enclose the tissue to be stapled. Since the surgical site in meniscal repair is usually quite small and crowded, the use of bulky instruments for driving staples is not practical.

The need, therefore, exists for an improved method and apparatus for repairing meniscal tissue which can reduce the time necessary to perform the procedure and improve the accuracy and consistency of applying fasteners across the meniscal tear.

SUMMARY OF THE INVENTION

The present invention provides a novel device for driving surgical fasteners to tissues such as the fibro-cartilage disk in the knee known as the menisci. The novel device obviates the disadvantages encountered in the prior art and provides a driving mechanism which applies tacks or fasteners in the form of darts to repair meniscal tears which controls the force necessary for applying the fasteners. Furthermore, the strength of the surgeon is not a factor, since the device is spring-loaded which allows the surgeon to estimate the depth of penetration and the force required to apply the fastener to that depth. In addition, the device is compact and lightweight, allowing for use at crowded surgical sites such as arthroscopic surgical procedures performed on the knee to repair torn meniscal tissue.

More particularly, the present invention provides a device for driving surgical fasteners such as barbed tacks or darts which penetrate the tissue across the tear to pull the abutting surfaces of the tear into contact to facilitate healing. The present invention is a hand-held, lightweight mechanism which is spring loaded to provide varying driving forces depending on the depth of penetration required to surgically repair the tear. The device essentially comprises an enclosure which is provided with a gripping knob at one end which engages a trigger mechanism, and which tapers to a small tubular opening at the operating end to provide for the delivery of the surgical fastener to the surgical site. The opening at the operating end is preferably sized to frictionally secure the surgical fastener therein, so that the fastener remains in place until the driving mechanism is activated.

The driving device essentially comprises a spring activated piston which is secured to a transfer block, to which a second piston is secured for driving the fastener into the tissue. The gripping knob is connected to the piston shaft so that as the knob is retracted from the housing, the spring is compressed so that the driving piston is biased towards the operating end of the housing. The trigger device essentially comprises a pivotable latch member having a series of notches which engage the gripping knob to allow the surgeon to set the driving force as determined by the distance the piston and gripping knob are retracted from the housing.

In use, after the gripping knob is retracted and latched with the trigger member, a surgical dart or tack is positioned in the opening and is frictionally secured therein. After the surgeon incises the skin of the patient, the device is moved to the surgical site so that the tip of the dart or tack is placed on one side of the tear in the menisci. The surgeon then pivots the latch mechanism, thus firing the transfer block and discharge piston which contacts the surgical fastener to drive it into the tissue across the tear to secure the two sides of the tear together. This procedure may be repeated any number of times to properly secure the tear along its length.

The device of the present invention may be constructed of any sterilizable material, such as high impact plastic or stainless steel. The device may be disposable after use to eliminate the necessity for resterilization of the device.

BRIEF DESCRIPTION OF THE DRAWINGS

The foregoing features of the present invention will become more readily apparent and may be understood by referring to the following detailed description of an illustrative embodiment of the device for driving surgical fasteners, taken in conjunction with the accompanying drawings, in which.

DETAILED DESCRIPTION OF THE PREFERRED EMBODIMENTS

Figure 1:
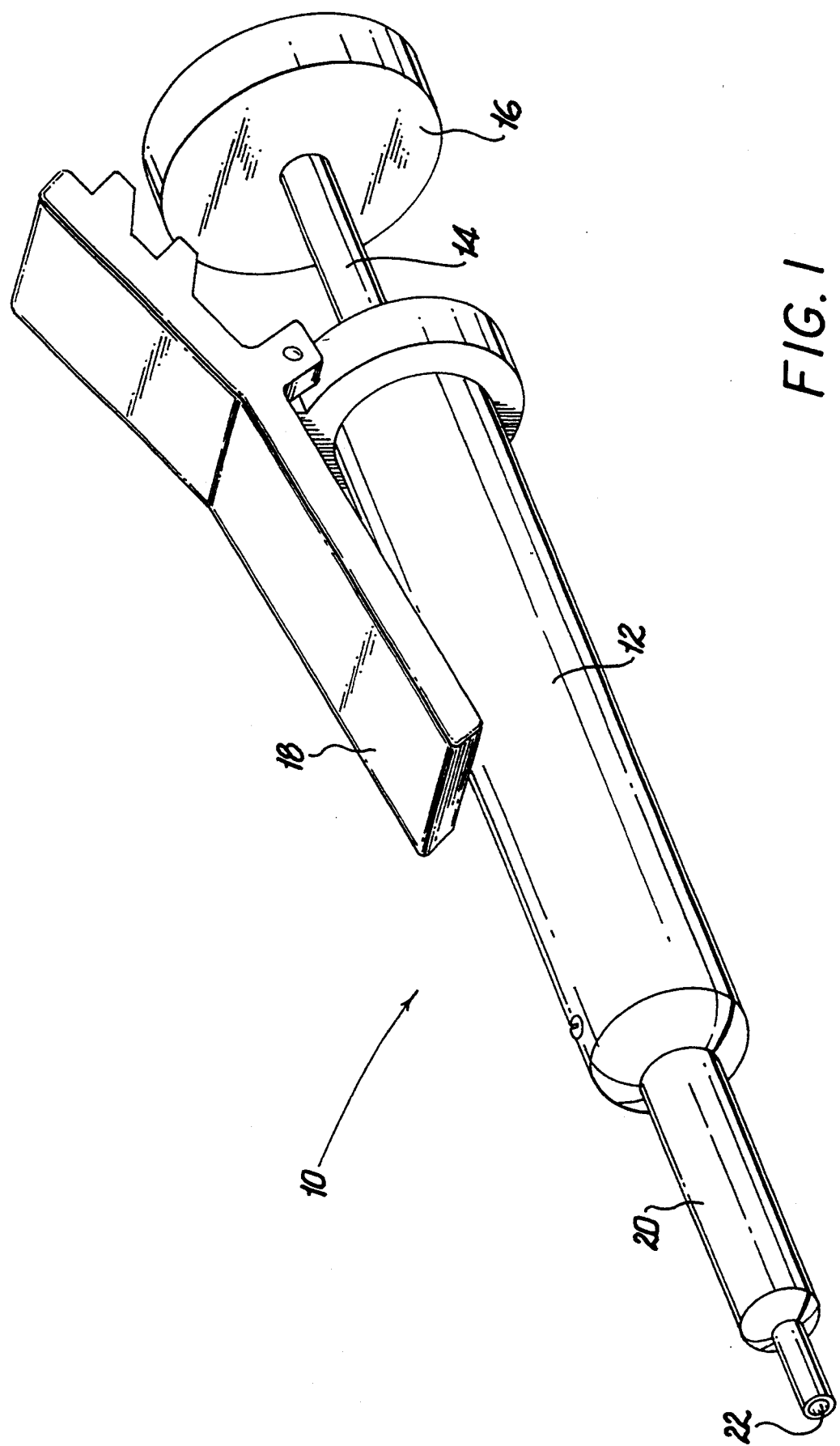
FIG. 1 illustrates a perspective view of the surgical fastener driving device of the present invention.

Referring now in specific detail to the drawings, in which like reference numerals identify similar or identical elements throughout the several views, FIG. 1 illustrates the device for driving surgical fasteners such as barbed tacks or barbed darts of the present invention. Fastener driving device 10 has a generally tubular shape and includes a main housing 12 from which extends a piston shaft 14 which terminates in a gripping knob 16. Shaft 14 extends generally coaxially through housing 12, and essentially extends through opening 22 at the distal end of the housing. Housing 12 tapers at the discharge end 20, for firing a fastening member such as a dart or tack from the opening 22. A pivotable latching member 18 is provided which engages gripping knob 16 when the knob 16 and shaft 14 are retracted from housing 12 to hold shaft 14 in the loaded position.

Figure 2:
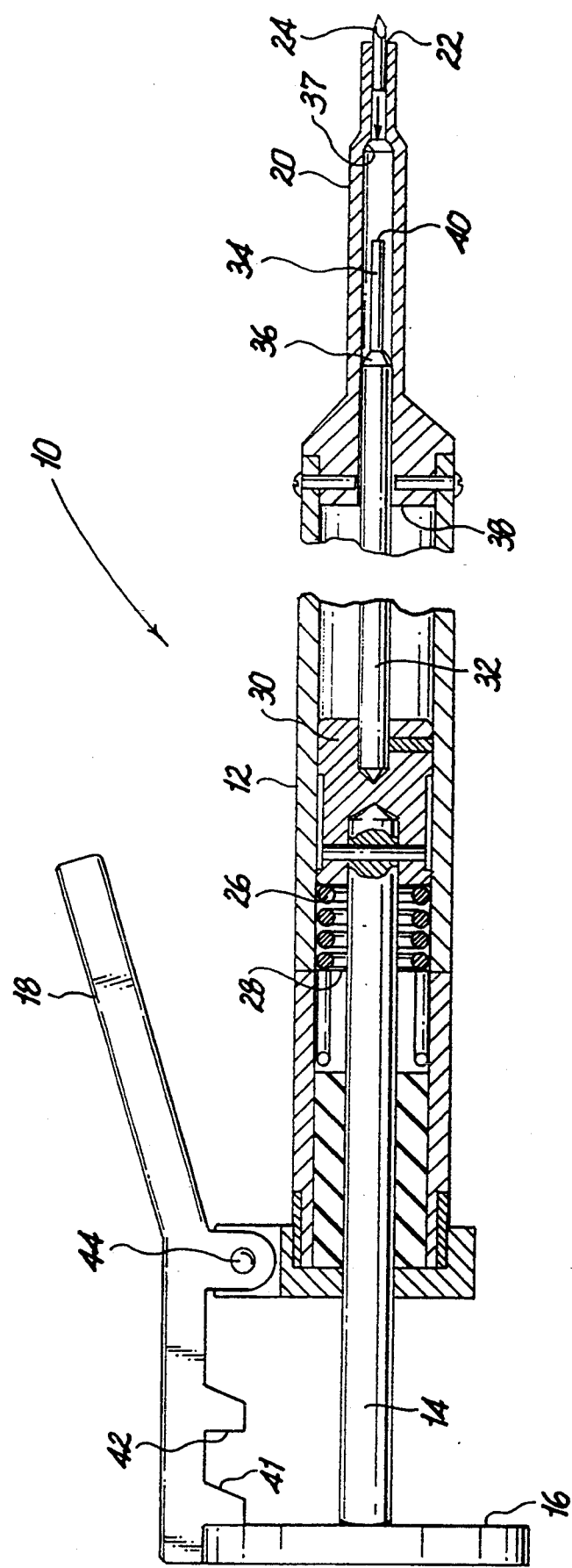
FIG. 2 illustrates a side cut-away view of the device of the present invention in the loaded condition.

FIG. 2 shows device 10 in a side cut-away view to illustrate the various components which comprise device 10. FIG. 2 shows device 10 in the loaded condition, in which knob 16 and shaft 14 are fully retracted from housing 12. As knob 16 is retracted, it slides over ramp portions 41 of latching member 18 to engage locking faces 42. Locking faces 42 maintain device 10 in the loaded condition until latch member 18 is pivoted about pivot point 44 to release piston shaft 14 to fire a fastener, as will be described below.

Piston shaft 14 passes generally coaxially through housing 12 and is secured to transfer block 30 which is generally constructed of rigid plastic or rubber material. Transfer block 30 is biased in the direction of opening 22 by spring member 26, which is positioned against spring wall 28. Connected at an opposite end to transfer block 30 is discharge piston shaft 32 which passes through the remainder of housing 12 and into discharge end 20, which tapers to opening 22. A stop member 38 is provided to limit the forward travel of transfer block 30 towards opening 22.

Shaft 32 tapers at taper portion 36 to form contact member 34, which is provided with a contact end 40 for engaging a proximal end of fastener member 24. Taper portion 36 engages taper portion 37 of discharge end 20 to limit the forward movement of the shaft of 32.

In use, knob 16 is withdrawn, along with piston shaft 14, from housing 12 and engages one of locking faces 42 of latching member 18 to secure device 10 in the loaded condition. As seen in FIG. 2, spring member 26 is compressed as knob 16 is withdrawn to engage one of locking faces 42. Discharge shaft 32 is retracted as shown, and a fastening member 24 is frictionally positioned and secured in opening 22 for use during a surgical procedure. When the device is positioned adjacent a tear in the meniscus during the surgical procedure, latching member 18 is depressed to pivot about pivot point 44 to the position shown in FIG. 3 to release knob 16 from locking face 42. Spring member 26 forces transfer block 30 in the direction towards opening 22 (see arrow A), so that contact end 40 of contact member 34 engages the proximal end of fastener member 24 to drive the fastener from opening 22. As transfer block 30 travels forward, it engages stop member 38, while taper portion 36 engages taper portion 37 to halt the forward movement of the transfer block 30. Latching member 18 may be provided with a biasing spring which causes it to return to the position shown in FIG. 2 after the surgeon releases the pivot pressure.

Figure 3:
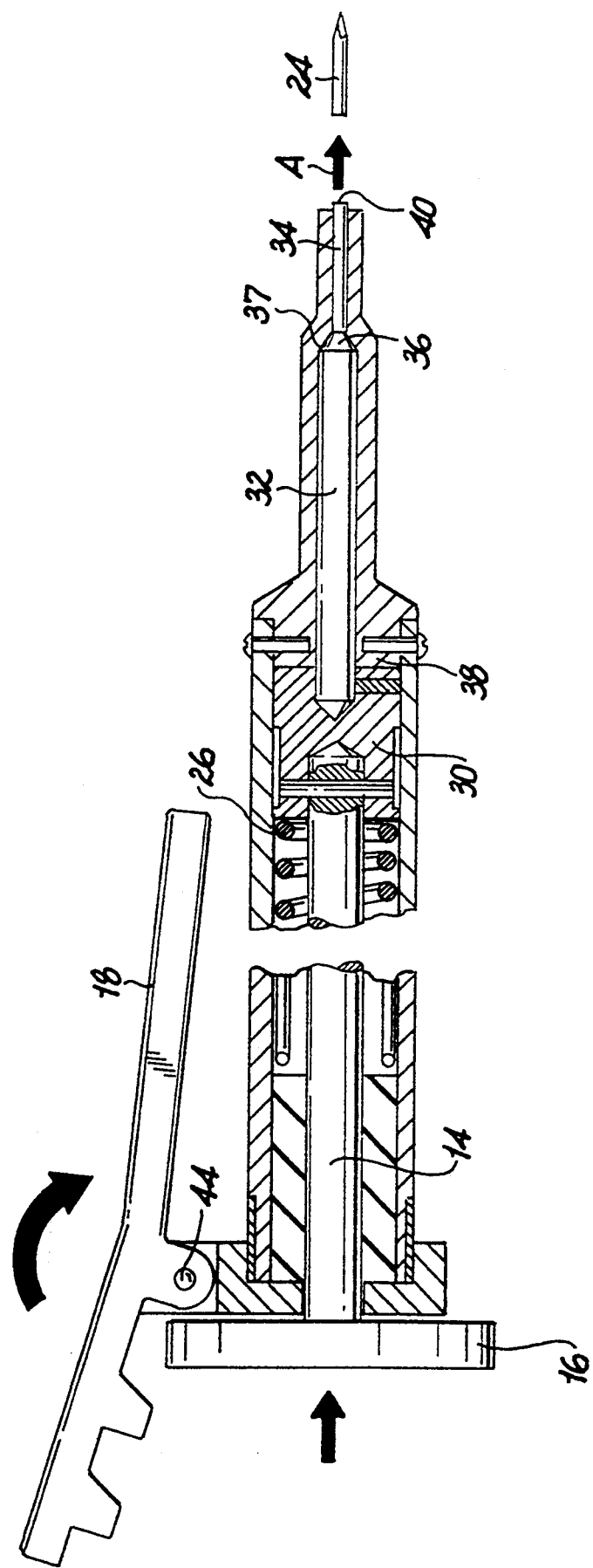
FIG. 3 illustrates a side cut-away view of the device of the present invention in the fired position.

FIG. 3 illustrates a cut-away view of the device as shown in the fired position. Spring member 26 has expanded from its compressed state as shown in FIG. 2, and transfer block 30 has engaged stop member 38 to limit its forward movement. Taper portions 36 and 37 also engage to stop the forward movement of transfer block 30. The force of movement of the transfer block 30, as well as that of shaft 32 engaging fastening member 24, drives fastening member 24 with sufficient force and velocity out of opening 22 and into the tissue to secure the fastener therein.

Although only a single dart 24 is shown loaded in the device 10, in an alternate embodiment, a cartridge can be provided to stock a plurality of darts to allow more rapid sequential firing of a series of darts across a meniscal tear.

Figure 4:
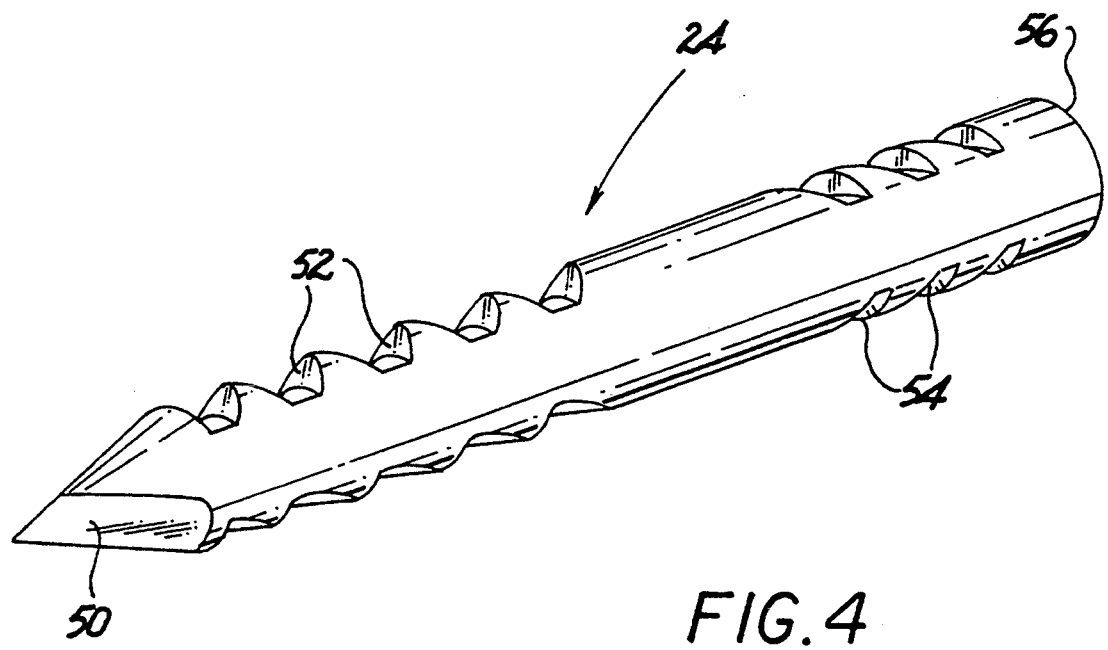
FIG. 4 illustrates a perspective view of a dart or fastener for use with the present invention.
Figure 5:
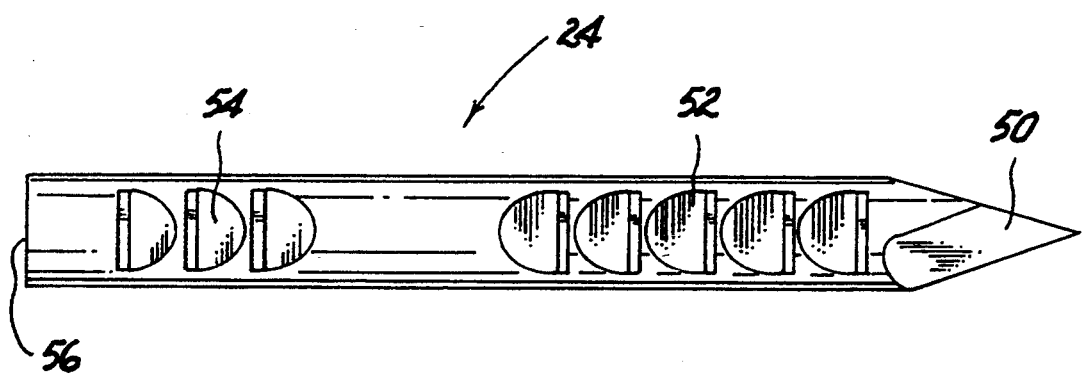
FIG. 5 illustrates a top plan view of the dart of FIG. 4.

FIGS. 4 and 5 illustrate a fastening member for use with the device of the present invention. Fastening member 24 is shown in the shape of a dart and is provided with a pointed tip 50, illustratively a trocar-type tip, to facilitate penetration of the fastener 24 through the meniscal tissue. A plurality of rearwardly directed barbs 52 are provided which permit forward movement of fastener 24 through the tissue, but which prevent backing off of fastener 24 out of the tissue once the fastener 24 is secured therein. Forwardly directed barbs 54 are provided to limit penetration of the fastener 24 through the tissue, and to prevent forward movement of the fastener 24 after implantation. Thus, the barbs retain the fastener 24 in position across the meniscus. The provision of rearwardly directed barbs 52 and forwardly directed barbs 54 also function to pull the tissue sections on opposite sides of the tear toward each other and to hold them closer together to promote healing. A flat, butt end 56 is provided which is engaged by contact end 40 of shaft 32 to drive fastener 24 from device 10 with sufficient velocity to penetrate the meniscus.

Figure 6:
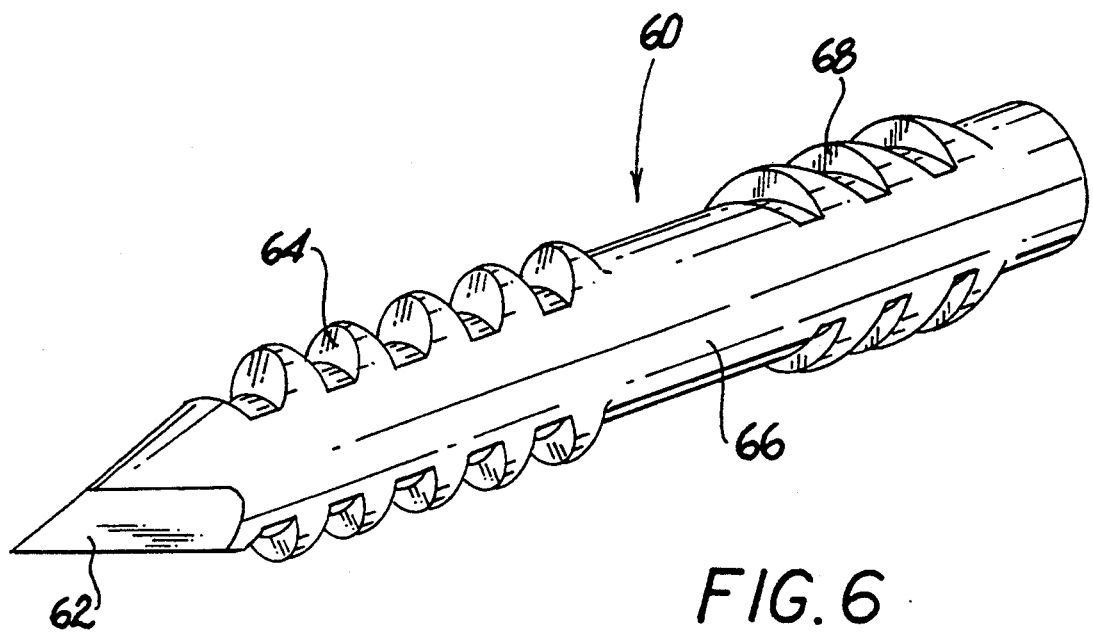
FIG. 6 illustrates a perspective view of an alternate embodiment of the dart for use with the device of the present invention.
Figure 7:
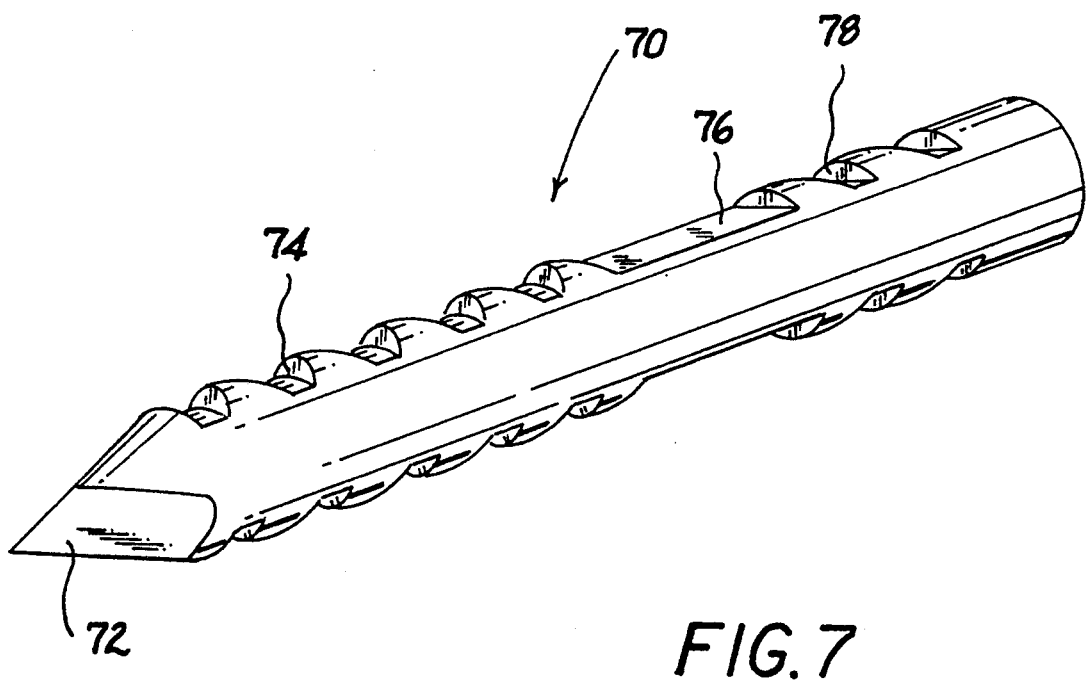
FIG. 7 illustrates a perspective view of a further alternate embodiment of a dart for use with the device of the present invention.

FIGS. 6 and 7 illustrate alternate embodiments of fastener 24 which may be used with device 10 of the present invention. Fastener 60 is provided with a pointed tip 62 to facilitate penetration through tissue, and is provided at a forward end with raised barbs 64 which allow penetration in a forward direction but which limit or prohibit movement in a reverse direction after fastener 60 is anchored in the tissue. Shank portion 66 joins barbs 64 with forwardly directed barbs 68. Barbs 68 limit penetration of fastener 60 through the tissue. Barbs 64 and 68 also pull the tissue sections together in a similar manner as barbs 52 and 54 described above.

FIG. 7 illustrates fastener 70, which is identical to fastener 24 of FIG. 4, except for the provision of land portion 76 on the shank. Land portion 76 joins rearwardly directed barbs 74 with forwardly directed stop barbs 78, which limit penetration of fastener 70 through the tissue.

Although the fasteners are shown with separate barbs formed on the top and on the bottom surfaces, in an alternate embodiment, the front and rear barbs can each extend around the entire circumference of the fastener. Additionally, a fewer or larger number of barbs than shown in the drawings could be provided so long as they achieve the functions described above.

The fasteners are preferably composed of a resorbable material which will gradually be decomposed and assimilated by the body so they do not need to be removed from the meniscus after insertion. Examples of resorbable materials which can be utilized include homopolymers or copolymers of lactide, glycolide, trimethylene carbonate, polyorthoesters, polyethylene oxide or other bioabsorbable polymer materials or blends of these respective polymers. One preferred material is made of a copolymer of lactide and glycolide made from approximately 18% m glycolide and 82% m lactide. Although various size fastening members can be utilized, in one preferred embodiment, the fastening member has a length of approximately between 0.40 inches and 0.50 inches, and a diameter of between 0.025 inches and 0.050 inches. However, these dimensions are provided by way of example only as fasteners of other dimensions are also contemplated by the present invention.

Figure 8:
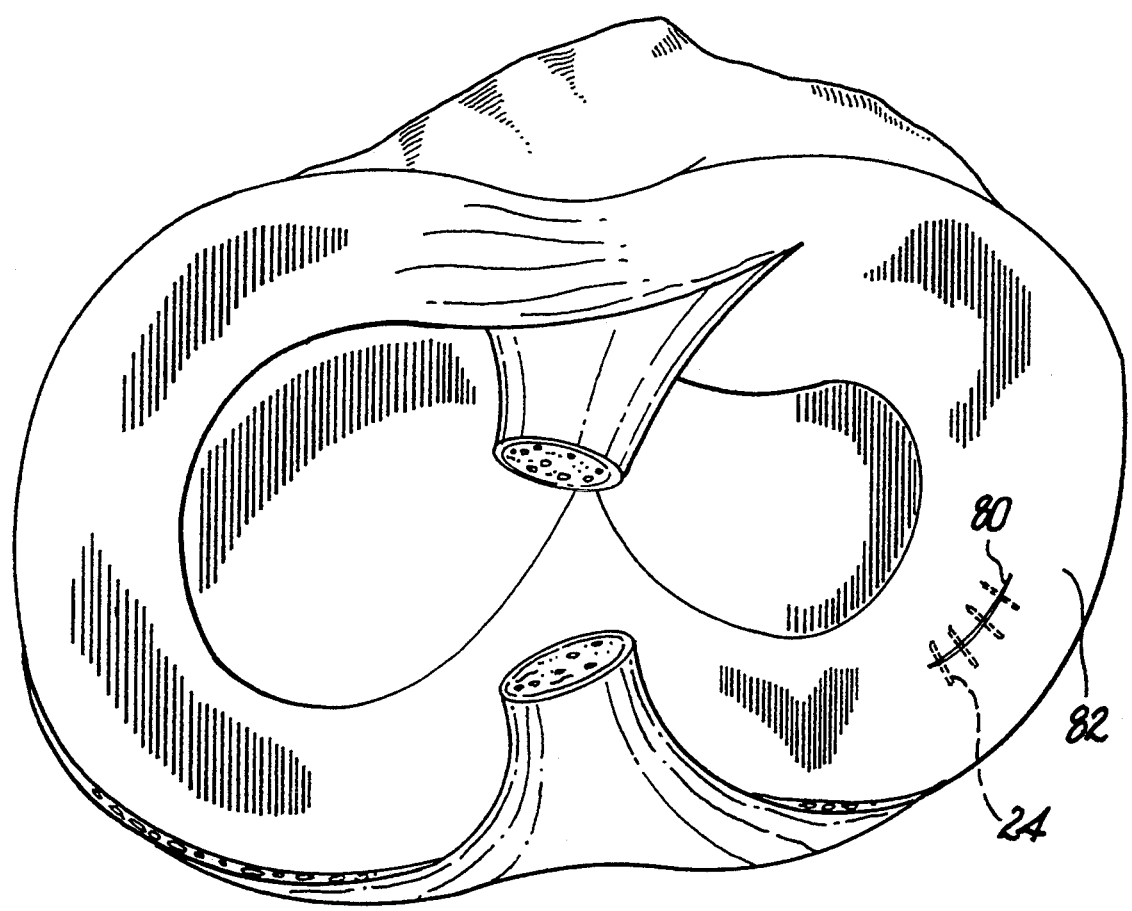
FIG. 8 illustrates a top perspective view of a knee showing the meniscus having a series of darts implanted across the tear.

FIG. 8 shows the fastening members 24 inserted across the tear in the meniscus to hold the edges of the tear in abutting relation. In use, device 10 is placed against a first side of tear 80 in meniscus 82 so that as the piston is fired, a fastening member 24 is fired through the meniscus 82 across tear 80 to secure the edges of the tear.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A device for driving surgical fasteners into tissue, comprising:
   an elongated housing member having a distal end and a proximal end, said housing member including an opening at said distal end for positioning a surgical fastener therein,
   a piston shaft extending through said housing member from said proximal end, said piston shaft being movable from a rest position in which a driving end of said piston shaft extends through said opening at said distal end of said housing member, to a loaded position in which said piston shaft is retracted into said housing member at said distal end of said housing member to permit positioning of a surgical fastener therein,
   a spring for biasing said piston shaft towards said distal end of said housing member when said piston shaft is in said loaded position,
   a gripping member disposed at said proximal end of said housing member and attached to a proximal end of said piston shaft for moving said piston shaft from said rest position to said loaded position, and
   a pivotable trigger device movable from a first position in which said trigger device locks said piston shaft in said loaded position to a second position to release said piston shaft, wherein movement of said piston shaft from said loaded position to said rest position drives a fastener positioned in said opening out of said housing member and into tissue.

2. A device according to claim 1, wherein said housing member is tubular in shape and tapers at said distal end to said opening.

3. A surgical repair device according to claim 1, wherein said distal end of said housing member tapers to an opening for accepting said fastener, said opening having a diameter substantially identical to an outer diameter of said fastener to frictionally engage said fastener therein.

4. A device according to claim 1, wherein said spring is at rest when said piston shaft is in said rest position and said spring is compressed when said piston shaft is in said loaded position.

5. A device according to claim 1, wherein said gripping member comprises a knob to facilitate retracting said piston shaft from said rest position into said loaded position.

6. A device according to claim 1, wherein said trigger device engages said gripping member to hold said piston shaft in said loaded position.

7. A device according to claim 1, wherein said trigger device engages said piston shaft by means of a notch in said trigger device to hold said piston shaft in said loaded position.

8. A device according to claim 1, wherein said trigger device includes means to provide for incrementally increasing the distance said piston shaft is retracted to said loaded position.

9. A device according to claim 8, wherein said trigger device means for incrementally increasing the distance comprises a plurality of notches on said trigger device for engaging said gripping member at increasing distances.

10. A device according to claim 1, wherein said trigger device is biased towards engagement with said piston shaft.

11. A device according to claim 1, wherein said piston shaft is secured to a transfer block, said transfer block engaging said spring to bias said piston shaft toward said rest position.

12. A device according to claim 1, wherein said piston shaft comprises two shafts, each shaft secured to and extending from a transfer block, a first shaft secured to said gripping member and a second shaft comprising said driving end.

13. A device according to claim 12, wherein said transfer block engages said spring to bias said piston shaft toward said rest position.

14. A device according to claim 1, wherein said surgical fastener comprises a rod having a plurality of barbs along its length, said rod having a point at one end and a blunt end at a second end for engaging said distal end of said piston shaft.

15. A device according to claim 1, wherein said surgical fastener is frictionally held in said opening at said distal end of said housing member prior to firing.

* * * * *